United States Patent [19]
Itoh et al.

[11] Patent Number: 5,389,786
[45] Date of Patent: Feb. 14, 1995

[54] METHOD OF QUANTITATIVE DETERMINATION OF DEFECT CONCENTRATION ON SURFACES

[75] Inventors: Noriaki Itoh, Nagoya; Yasuo Nakai, Kani; Ken Hattori, Tokyo; Akiko Okano, Toyota, all of Japan

[73] Assignee: President of Nagoya University, Nagoya, Japan

[21] Appl. No.: 46,758

[22] Filed: Apr. 15, 1993

[30] Foreign Application Priority Data

Oct. 6, 1992 [JP] Japan .................................. 4-267469

[51] Int. Cl.⁶ ............................................. G01N 21/00
[52] U.S. Cl. .................................. 250/307; 250/423 P
[58] Field of Search .................... 250/306, 307, 423 R, 250/423 P

[56] References Cited

U.S. PATENT DOCUMENTS

| | | | |
|---|---|---|---|
| 4,733,073 | 3/1988 | Becker et al. | 250/288 |
| 4,740,692 | 4/1988 | Yamamota et al. | 250/282 |
| 4,988,879 | 1/1991 | Zare et al. | 250/423 P |
| 5,138,158 | 8/1992 | Ninomiya et al. | 250/305 |
| 5,146,088 | 9/1992 | Kingham et al. | 250/423 P |

Primary Examiner—Jack I. Berman
Assistant Examiner—James Beyer
Attorney, Agent, or Firm—Oblon, Spivak, McClelland, Maier & Neustadt

[57] ABSTRACT

The ablation threshold of a laser fluence with respect to the surface of a sample manufactured in a high vacuum chamber is determined by using the sample. The quantity of vacancy-type defects is determined by radiating a laser beam having a fluence slightly higher than the ablation threshold on the surface. At the same time, the quantities of adatom-type and kink-type defects are determined by radiating a pulsed laser beam having a fluence slightly lower than the ablation threshold on the surface repeatedly to obtain the relation between an emission yield and the number of laser pulses. The quantity of the adatom-type defects is obtained by determining the area (total quantity of emitted atoms) of a rapidly decreasing portion of the relation. The quantity of kink-type defects is obtained by determining a magnitude of an emission yield of a slowly decreasing portion of the relation.

3 Claims, 7 Drawing Sheets

METHOD OF QUANTITATIVE DETERMINATION OF DEFECT CONCENTRATION ON SURFACES

BACKGROUND OF THE INVENTION

1. Field of the Invention

The present invention relates to a method of quantitative determination of defect concentration on surfaces.

2. Description of the Related Art

In recent years, although the structure of a defect on a semiconductor surface can be observed through a scanning tunneling microscope, the quantitative defect concentration on the surface cannot be determined. There is no method for such quantitative measurement.

Surface defects influence the characteristics of an epitaxial growth film or the like. Therefore, demands have arisen for the development of a method of easily determining the quantitative surface defects.

SUMMARY OF THE INVENTION

It is an object of the present invention to provide a method of easily determining a quantitative surface defect concentration.

According to the present invention, there is provided a method of quantitative determination of defect concentration on surfaces, comprising the steps of:

determining an ablation threshold of a laser fluence with respect to a surface of a sample, manufactured in a high vacuum chamber; and determining a quantity of vacancy-type defects by radiating a laser beam having a fluence slightly higher than the ablation threshold on the surface and measuring a first emission yield $Y_1$, and determining quantities of adatom-type and kink-type defects by radiating a pulsed laser beam having a fluence slightly lower than the ablation threshold on the surface repeatedly to obtain a relation between second emission yield $Y_2$ and the number of laser pulses, the quantity of the adatom-type defects being obtained by determining an area under a first portion of the relation, and the quantity of the kink-type defects being obtained by determining a magnitude of the second emission yield $Y_2$ of a second portion of the relation, the first portion having a steeper negative slope than the second portion.

According to the principle of the present invention, in measurement of laser-induced atom emission, the quantity of surface defects is measured from the amount of emitted atoms on the basis of the fact that atoms are emitted through adatom-type defects, kink-type defects, and vacancy-type defects, respectively, when the laser fluence is low, intermediate, and high.

The quantity of adatom-type defects is determined by measuring the total quantity of emitted atoms because the defects are removed upon atom emission. In determining this total quantity, a known quantity of adatom-type defects is measured by a laser resonance ionization method, and calibration is performed by using the resultant data.

The quantity of vacancy-type defects is obtained by using an emission coefficient determined by a preliminary experiment on the basis of the relationship between the emission yield and the laser fluence. In this case, measurement is performed on the basis of the fact that the emission yield is proportional to the quantity of vacancy-type defects on the surface.

Similarly, the quantity of kink-type defects is obtained by using an emission coefficient determined on the basis of the relationship between the emission yield and the laser fluence.

Note that in measurement of vacancy-type and kink-type defects, calibration is performed on the basis of measurement of a known quantity of defects with a scanning tunneling microscope.

According to such a method, the quantity of surface defects, which cannot be measured by the prior art, can be measured.

According to the present invention, the quantities of all types of defects, i.e., adatom-type, kink-type, and vacancy-type defects, can be easily measured. That is, defects which can only be observed qualitatively by the prior art, can be quantitatively measured, thereby allowing quantitative evaluation of a surface.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

DETAILED DESCRIPTION OF THE PREFERRED EMBODIMENTS

Measurement Apparatus

Figure 1:
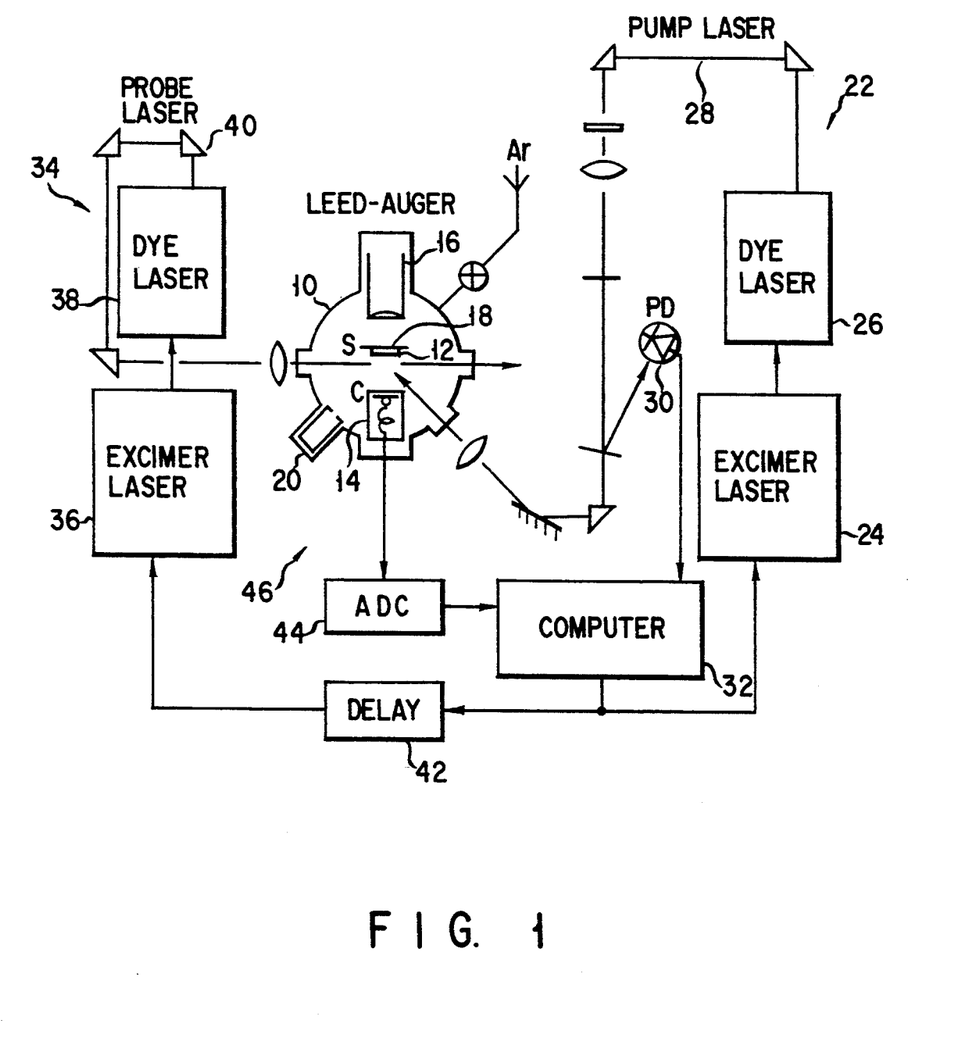
FIG. 1 is a block diagram showing a schematic arrangement of an apparatus for executing a method of quantitative determination of defect concentration on surfaces according to an embodiment of the present invention.

FIG. 1 shows an apparatus for executing a method of quantitative determination of defect concentration on surfaces according to an embodiment of the present invention.

A sample 12 is placed in a vacuum chamber 10. A channel plate or Channeltron 14 for counting atoms emitted from a sample is disposed on the front surface of the sample 12. A LEED (low-energy electron-diffraction)-Auger 16 for observing the upper surface of the sample 12 is disposed on the lower surface side of the sample 12. A sample holder 18 is rotatable and is rotated to direct the front surface of the sample 12 to the Channeltron 14 or to the LEED-Auger 16 depending on which of the two is used. In addition, an ion gun 20 for performing argon ion bombardment with respect to the surface of the sample 12 is disposed in the vacuum chamber 10.

A laser system 22 serving as a pump laser is disposed on the right side in FIG. 1. The laser system 22 includes an excimer laser 24, a dye laser 26 pumped by the excimer laser 24 to emit a laser having a wavelength of nearly 600 nm, an optical system 28 for guiding a laser beam from the dye laser 26 to the sample 12, and a photodetector 30 for measuring the fluence of the laser beam emitted from the dye laser 26. The laser beam emitted from the dye laser 26 passes through the optical system 28 to be incident on the surface of the sample 12 at an angle of 45°. This laser beam is a 28-ns pulse-like laser beam having a spot size of 0.5 mm. The pulse period of the laser beam is controlled by a computer 32. The laser beam emerging from the laser system 22 is radiated on the surface of the sample 12 to cause emission of atoms from the surface of the sample 12. Note that an output from the photodetector 30 is supplied to the computer 32, so that the fluence of the laser beam incident on the surface of the sample 12 is stored.

A laser system 34 serving as a probe laser is disposed on the left side in FIG. 1. This laser system 34 includes an excimer laser 36, a dye laser 38 pumped by the excimer laser 36, and an optical system 40 for guiding a laser beam from the dye laser 38 to the surface of the sample 12. The laser beam emitted from the dye laser 38 passes through the optical system 40 to propagate parallel to the surface of the sample 12 at a distance of 2.0 mm. This laser beam is a 28-ns pulse-like laser beam having a spot size of about 1.0 mm. The period of the laser beam is controlled by the computer 32.

The probe excimer laser pulse is delayed by a delay circuit 42, so that the laser beam emerging from the laser system 34 is supplied parallel to the surface of the sample 12 with a delay of 3.3 $\mu$s with respect to the laser beam emerging from the laser system 22. That is, the laser beam from the laser system 34 is supplied parallel to the surface of the sample 12 after the laser beam from the laser system 22 is radiated on the surface of the sample 12 and atoms are emitted from the surface of the sample 12. As a result, atoms emitted from the surface of the sample 12 are ionized to be detected. A resonance-ionization method is used in this detection method.

The atoms ionized by the resonance-ionization method are detected by the Channeltron 14. The resultant current is analog/digital-converted by an ADC 44. The output from the ADC 44 is supplied to the computer 32. As a result, the number of emitted atoms is counted to obtain a yield Y of the emitted atoms. A system constituted by the Channeltron 14, the ADC 44, and the computer 32 will be referred to as a measurement system 46 hereinafter.

Measurement Process

Figure 2:
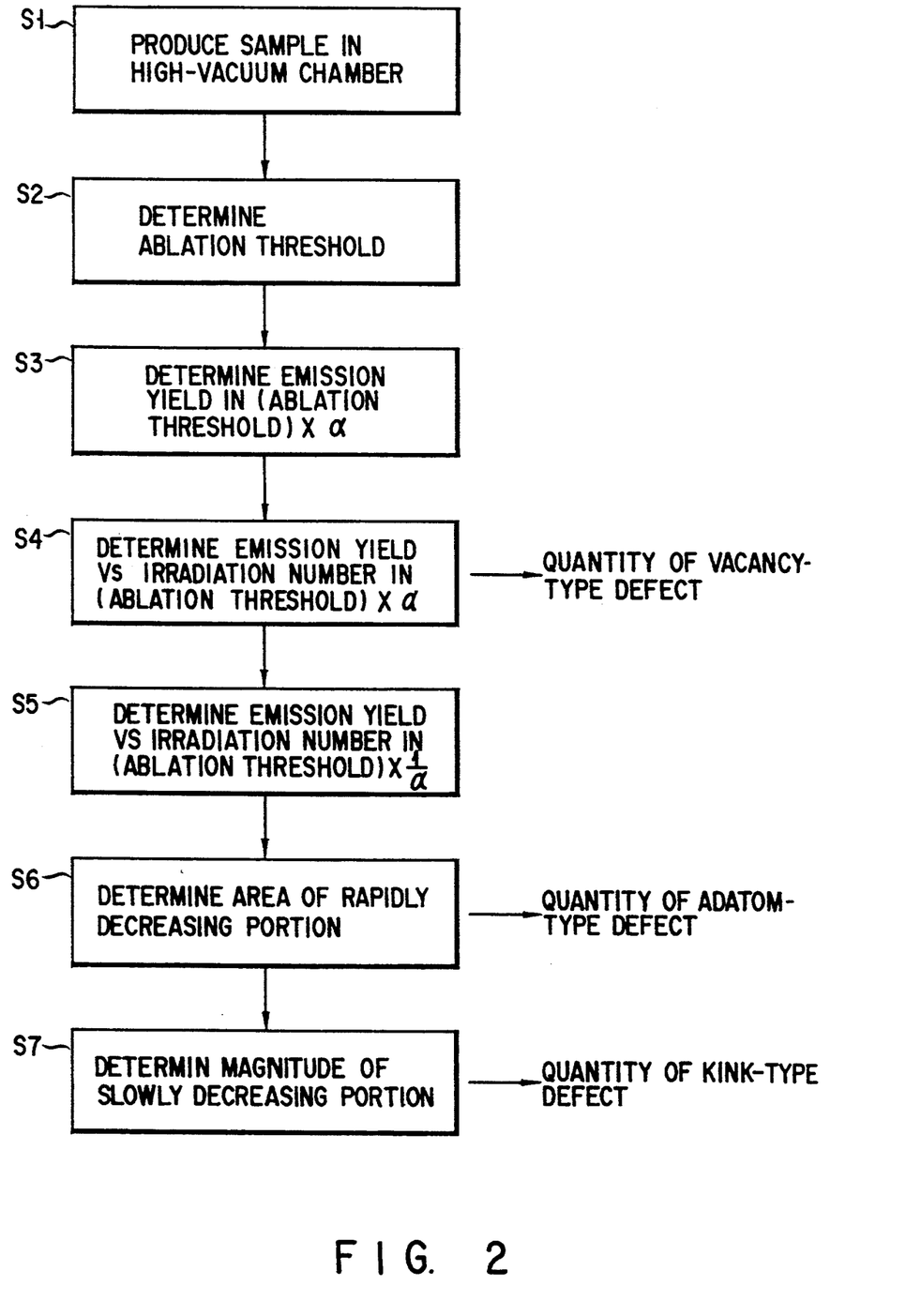
FIG. 2 is a flow chart showing a procedure based on the method of quantitative determination of defect concentration on surfaces according to the embodiment of the present invention.

An embodiment of the method of quantitative determination of defect concentration on surfaces will be described next with reference to FIG. 2.

In step S1, a sample 12 is manufactured in the vacuum chamber 10. The ion gun 20 is used to radiate 0.5-key argon ions on the manufactured sample 12 at a beam current of 2 to 3 $\mu$A for 30 min, thus cleaning the surface of the sample 12. The sample 12 is annealed thermally at 500° to 600° C. at intervals of 10 min by using a heat source (not shown) arranged on the sample holder 18.

In step S2, an ablation threshold for the sample 12 is determined. The ablation threshold is a laser fluence above which formation of a vacancy-type defect is started, specifically, a laser fluence at which the probability that an atomic bond near a vacancy-type defect is broken by one laser pulse is almost unity. Below the ablation threshold, atoms are emitted from only adatom-type and kink-type defects. However, above the ablation threshold, a vacancy-type defect is the source of the emission. Therefore, by properly determining this ablation threshold, measurement of the quantity of adatom-type and kink-type defects can be separated from measurement of the quantity of vacancy-type defects.

Figure 3A:
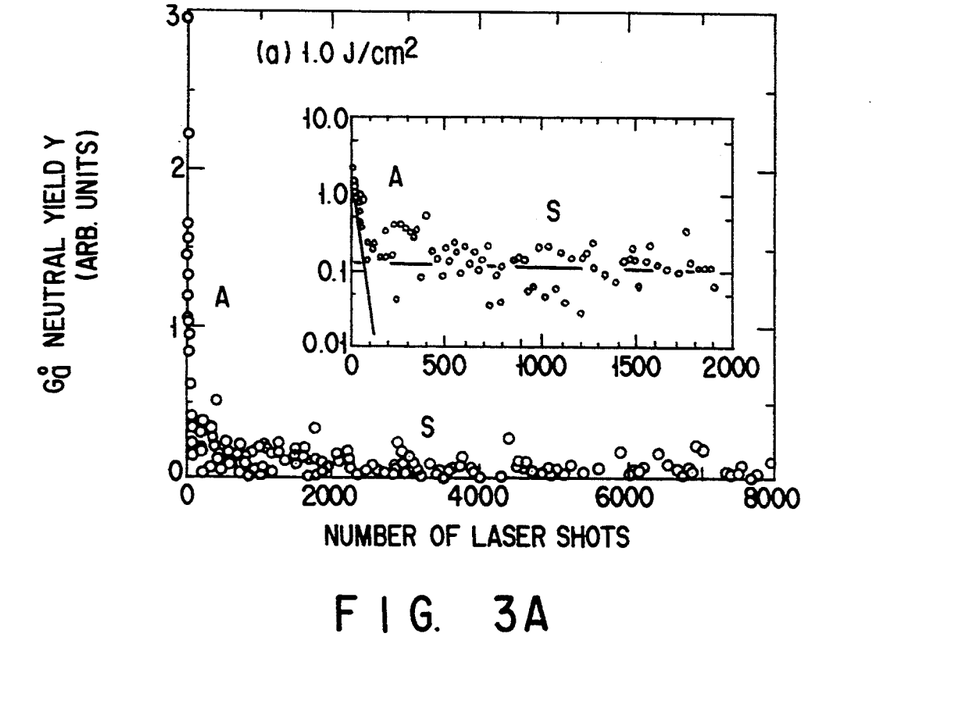
FIG. 3A is a graph showing the relationship between the number of laser shots and the emission yield from the GaP (110) surface in a case wherein the laser fluence is set to be 1.0 J/cm$^2$.
Figure 3B:
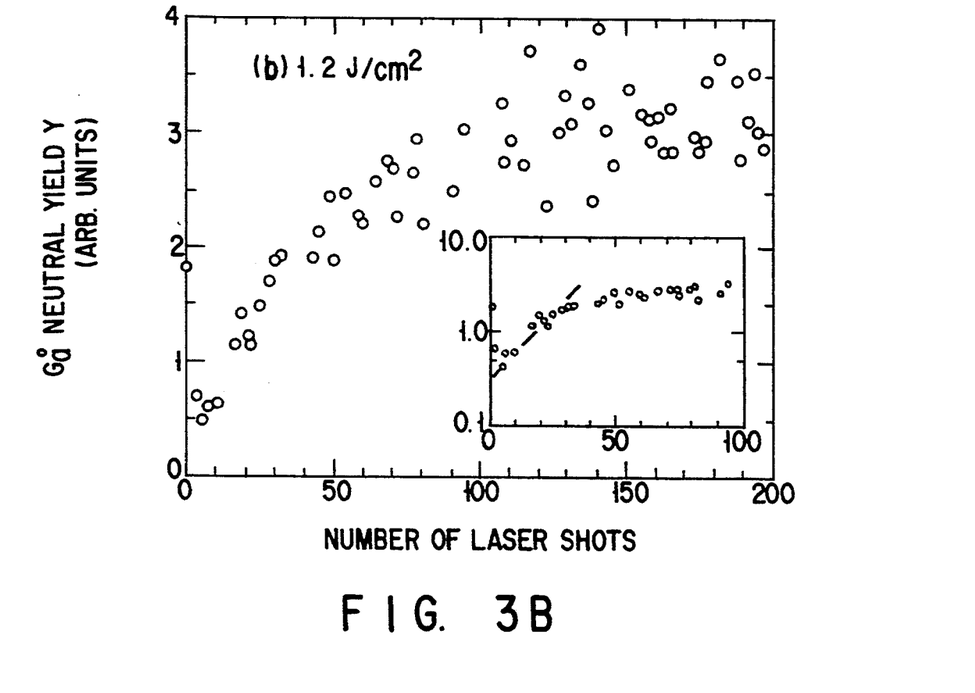
FIG. 3B is a graph showing the relationship between the number of laser shots and the emission yield in a case wherein the laser fluence is set to be 1.2 J/cm$^2$.

An ablation threshold is determined in the following manner. A pulse-like laser beam is radiated on the surface of the sample 12 by using the laser system 22. The yield Y of atoms emitted from the surface of the sample 12 is measured by using the laser system 34 and the measurement system 46. FIGS. 3A and 3B respectively show measurements of emission yields using the fluence of a laser beam radiated on the surface of the sample 12 as an index. FIG. 3A shows the relationship between the number of laser shots and the emission yield Y of Ga atoms in a case wherein the laser fluence is set to be 1.0 J/cm$^2$. FIG. 3B shows the relationship between the number of laser shots and the emission yield Y of Ga atoms in a case wherein the laser fluence is set to be 1.2 J/cm$^2$.

Referring to FIG. 3A, the region corresponding to reference symbol A indicates the quantity of Ga atoms emitted from adatom-type defects, and the portion corresponding to reference symbol S indicates the quantity of Ga atoms emitted from kink-type defects. That is, a laser fluence of 1.0 J/cm$^2$ does not cause the emission from a vacancy-type defect and hence is lower than the ablation threshold.

The dependence of the emission yield Y of Ga atoms on the number of laser shots, which is shown in FIG. 3B, is obtained at a laser fluence of 1.2 J/cm$^2$. This dependence on the number of laser shots is totally different from that shown in FIG. 3A. FIG. 3B shows that vacancy-type defects are the source of the emission at this laser fluence. Therefore, a laser fluence of 1.2 J/cm$^2$ is higher than the ablation threshold.

In this manner, the dependence of the emission yield Y on the number of laser shots is obtained while the laser fluence is changed, and the laser fluence at which the dependence on the number of laser shots changes is obtained. The obtained laser fluence is then set to be an ablation threshold.

Above the ablation threshold, vacancy-type defects on the surface of the sample 12 are the source of the emission. It is empirically known that the number of atoms emitted is proportional to the quantity of vacancy-type defects which are originally present on the surface of the sample 12. Therefore, the quantity of original vacancy-type defects can be determined by measuring the number of atoms emitted above the laser ablation threshold. In steps S3 and S4, the quantity of vacancy-type defects is measured on the basis of the this knowledge.

In step S3, a laser beam having a fluence of (ablation threshold)$\times\alpha$ is radiated on the surface of the sample 12 repeatedly by using the laser system 22 to obtain the emission yield Y by using the laser system 34 and the measurement system 46. Assume that $\alpha$ is about 1.1. That is, the radiated laser beam has a fluence slightly higher than the ablation threshold.

In step S4, the quantity of vacancy-type defects is determined on the basis of the rate of increase in the emission yield Y with respect to the number of laser shots. If an emission coefficient $q_r$ is used to indicate the quantity of vacancy-type defects, and the laser fluence, the exponent, and the quantity of defects are represented by $\phi$, n, and $N_r$, respectively, the emission yield Y is given by $$Y = q_r \phi^n N_r \qquad (1)$$

Figure 4:
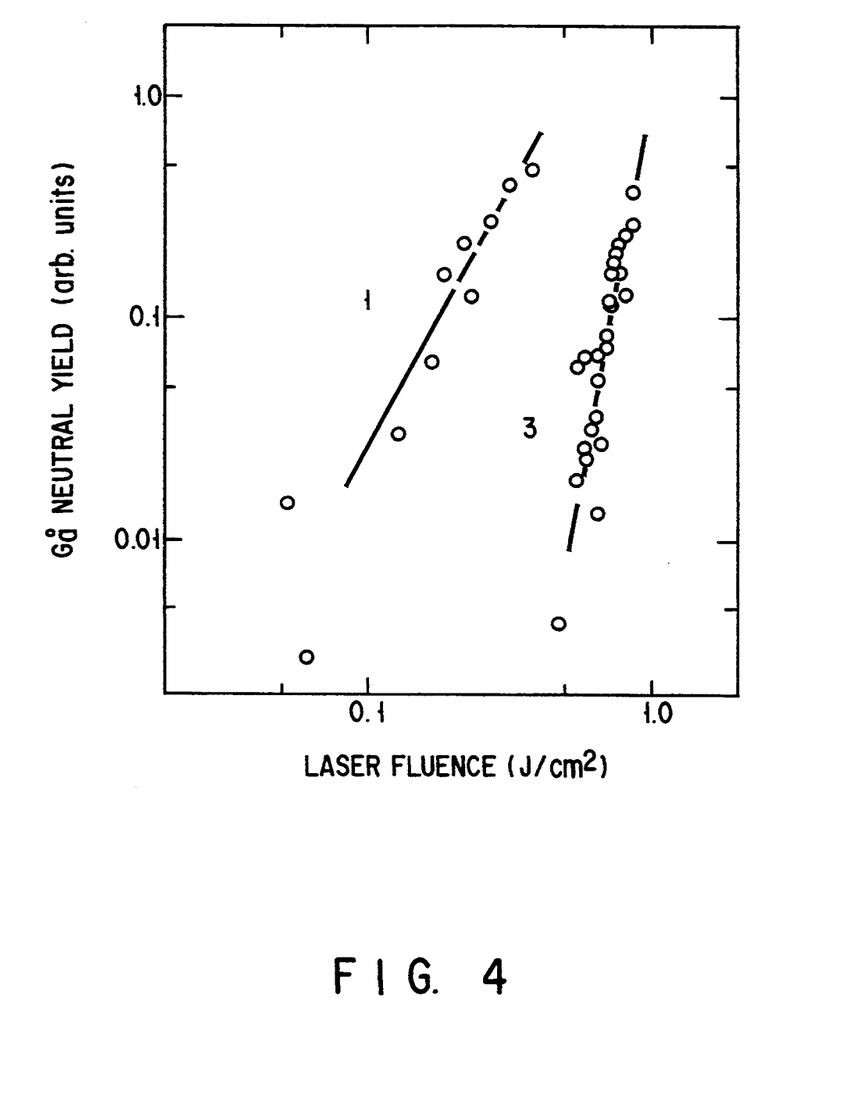
FIG. 4 is a graph showing the relationship between the laser fluence and the emission yield.

The emission coefficient $q_r$ and the exponent n are determined by a preliminary experiment in advance according to equation (1). In this preliminary experiment, a scanning tunneling microscope (STM; not shown) is scanned over a wide range on the sample 12 to determine the quantity $N_r$ of vacancy-type defects. The emission yield Y is measured while the laser fluence $\phi$ is changed within a range higher than the ablation threshold. When the logarithms of both the sides of equation (1) are obtained, a curve is plotted as in the graph shown in FIG. 4. The exponent n is determined from the slope of this curve, and the emission coefficient $q_r$ is determined from the intersecting point between the curve and the ordinate. Since the value of the emission yield Y in an arbitrary unit obtained by the measurement in step S3 can be calibrated into an absolute value, the quantity $N_r$ of vacancy-type defects can be obtained by using equation (1).

In step S5, a laser beam having a fluence of (ablation threshold)/$\alpha$ is radiated on the surface of the sample 12 many times by using the laser system 22 to obtain the emission yield Y by using the laser system 34 and the measurement system 46. As described above, the value $\alpha$ is set to be about 1.1. That is, the radiated laser beam has a fluence slightly lower than the ablation threshold. When the laser beam having a fluence slightly lower than the ablation threshold is radiated in this manner, atoms are emitted from adatom-type and kink-type defects. The data obtained in this step indicates the relationship between the emission yield and the number of laser shots, and can be divided into a rapidly decreasing portion A and a slowly decreasing portion S, as shown in FIG. 3A.

In step S6, the area (total quantity of emitted atoms) of the rapidly decreasing portion A is obtained to determine the quantity of adatom-type defects. Note that the ordinate indicates values in an arbitrary unit and hence needs to be calibrated into absolute values. For this purpose, a predetermined quantity of Ga atoms, e.g., $10^{-4}$ ML (mono atomic layer), are caused to adhere to a silicon substrate, and a laser beam having the same fluence as that of the laser beam used in step S5 is radiated on the Ga atoms to emit all the Ga atoms. An area corresponding to the resultant graph is then calculated to determine the unit of the emission yield Y on the ordinate. Note that the quantity of Ga atoms caused to adhere to the silicon substrate is measured with a film thickness measurement unit (not shown) capable of measuring a thickness corresponding to about 0.1 ML, and interpolation is performed by using the adhesion time.

In step S7, the magnitude of the emission yield of the slowly decreasing portion S obtained in step S5 is determined to obtain the quantity of kink-type defects. Note that the quantity of kink-type defects is expressed by using an emission coefficient $q_s$, similar to the corresponding quantity of vacancy-type defects. That is, if the laser fluence, the exponent, and the quantity of defects are respectively represented by $\phi$, n, and $N_s$, the emission yield Y is given by $$Y = q_s \phi^n N_s \qquad (2)$$

The emission coefficient $q_s$ and the exponent n are determined by a preliminary experiment in advance according to equation (2). In this preliminary experiment, the scanning tunneling microscope (STM) is scanned over a wide range on the sample 12 to determine the quantity $N_s$ of kink-type defects. The emission yield Y is measured while the laser fluence $\phi$ is changed within a range lower than the ablation threshold. When the logarithms of both the sides of equation (2) are obtained, a curve is plotted as in the graph shown in FIG. 4. The exponent n is determined from the slope of this curve, and the emission coefficient $q_s$ is determined from the intersecting point between the curve and the ordinate. Since the value of the emission yield Y in an arbitrary unit obtained by the measurement in step S5 can be calibrated into an absolute value, the quantity $N_s$ of kink-type defects can be obtained by using equation (2).

In the above-described embodiment, the quantity of vacancy-type defects is measured first, and the quantities of adatom-type and kink-type defects are measured subsequently. However, the order of measurement is not limited to this. It will be obvious to those skilled in the art that measurement of the quantity of vacancy-type defects, measurement of the quantity of adatom-type defects, and measurement of the quantity of kink-type defects can be executed in a proper order.

Method of Improving Measurement Sensitivity

In the above description, atoms emitted by one pulse from the laser system 22 are ionized by the laser system 34, and the resultant ion current pulse is measured by the measurement system 46, thereby measuring the emitted atoms of $10^{-5}$ ML per pulse. In this case, the number of ions included in one ion current pulse is about $10^4$. If this method is replaced with a counting method to perform measurement in which an ion count in one ion current pulse is 0.1, the measurement sensitivity can be increased by $10^5$ times, and the maximum sensitivity can be set to be $10^{-10}$ ML.

Types of Defects

Figure 5A:
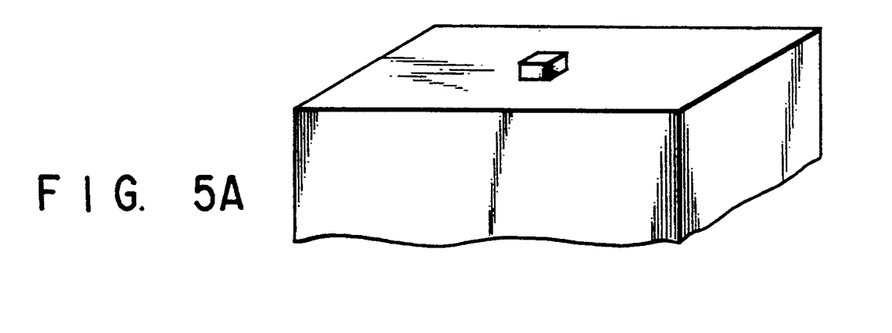
FIG. 5A is a schematic view showing the structure of an adatom-type defect.
Figure 5B:
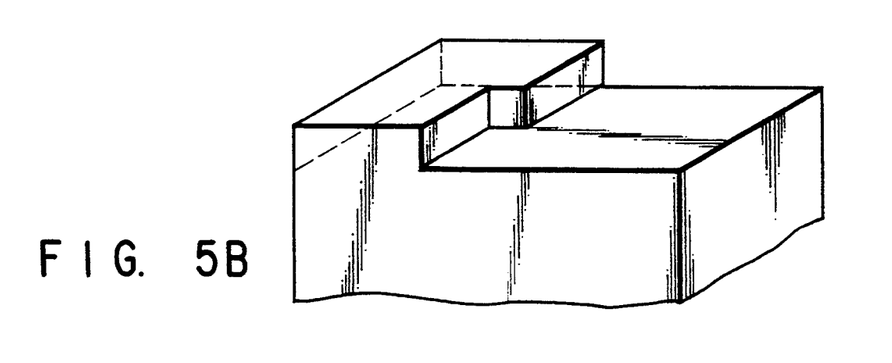
FIG. 5B is a schematic view showing the structure of a kink-type defect.
Figure 5C:
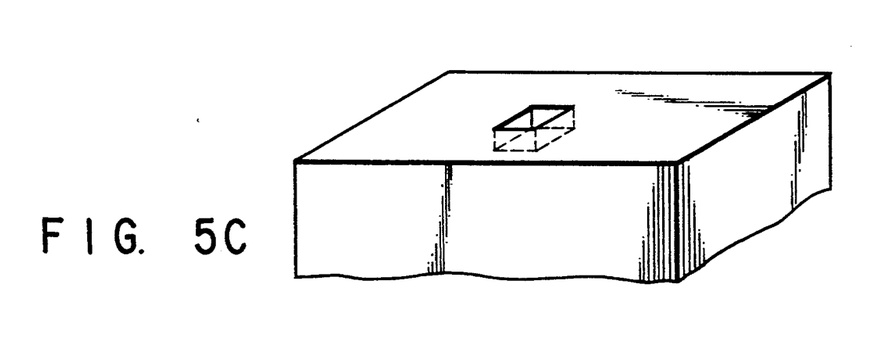
FIG. 5C is a schematic view showing the structure of a vacancy-type defect.

The adatom-type, kink-type, and vacancy-type defects described above are defects having structures such as those shown in FIGS. 5A, 5B, and 5C, respectively. The adatom-type defect is a defect adhering to a crystal surface and protruding therefrom. The kink-type defect is a defect in the form of a step on a crystal surface. The vacancy-type defect is a defect due to the absence of an atom at a lattice position on a crystal surface.

More specifically, there are weakly bonded atoms (to be referred to as WBAs hereinafter) near a defect. Defects can be classified into the following three types on the basis of a change accompanying the removal of one WBA near a defect:

(1) adatom-type defect: A defect adhering to a perfect crystal surface independently or in the form of an island. When this defect is removed, an almost perfect crystal surface appears.

(2) kink-type defect: when an atom is emitted from a defect, a similar defect is newly formed at a neighboring site. A kink in the form of a step on a crystal surface is an example of this type. This defect can be eliminated only by removing many portions protruding from the surface.

(3) vacancy-type defect: A defect whose defective region is enlarged when an atom is emitted from the defect.

Materials to which the Invention can be Applied

Materials to which the measurement method of the present invention can be applied must satisfy the following requirements:

(1) They must be nonmetallic materials. In nonmetallic materials, recombination of an electron-hole pair supplies energy corresponding to the width of a forbidden band to a lattice system.

(2) They must be materials in which an electron-hole pair is recombined only through a defect. Silver halides, alkali halides, alkaline-earth fluorides, $SiO_2$, and the like cannot be used because recombination of electron-hole pairs or excitons occurs when a perfect crystal is distorted.

(3) They must be polar crystals including no silicon. In nonpolar crystals such as silicon crystals, when a halogen of 1 ML is adsorbed in a crystal surface, a similar emission may be observed to perform the measurement of the present invention.

For example, materials to which the present invention can be applied are III–V Group compounds, II–VI Group compounds, ZnO, MgO, and CaO.

Laser Wavelength

A proper laser wavelength used in the method of the present invention will be described below. In the present invention, as described above, adatom-type, kink-type, and vacancy-type defects are measured. In order to remove adatom-type and kink-type defects from the surface of the sample 12 by irradiation with a laser beam, surface electron-hole pairs must be formed in as large a number as possible.

Figure 6:
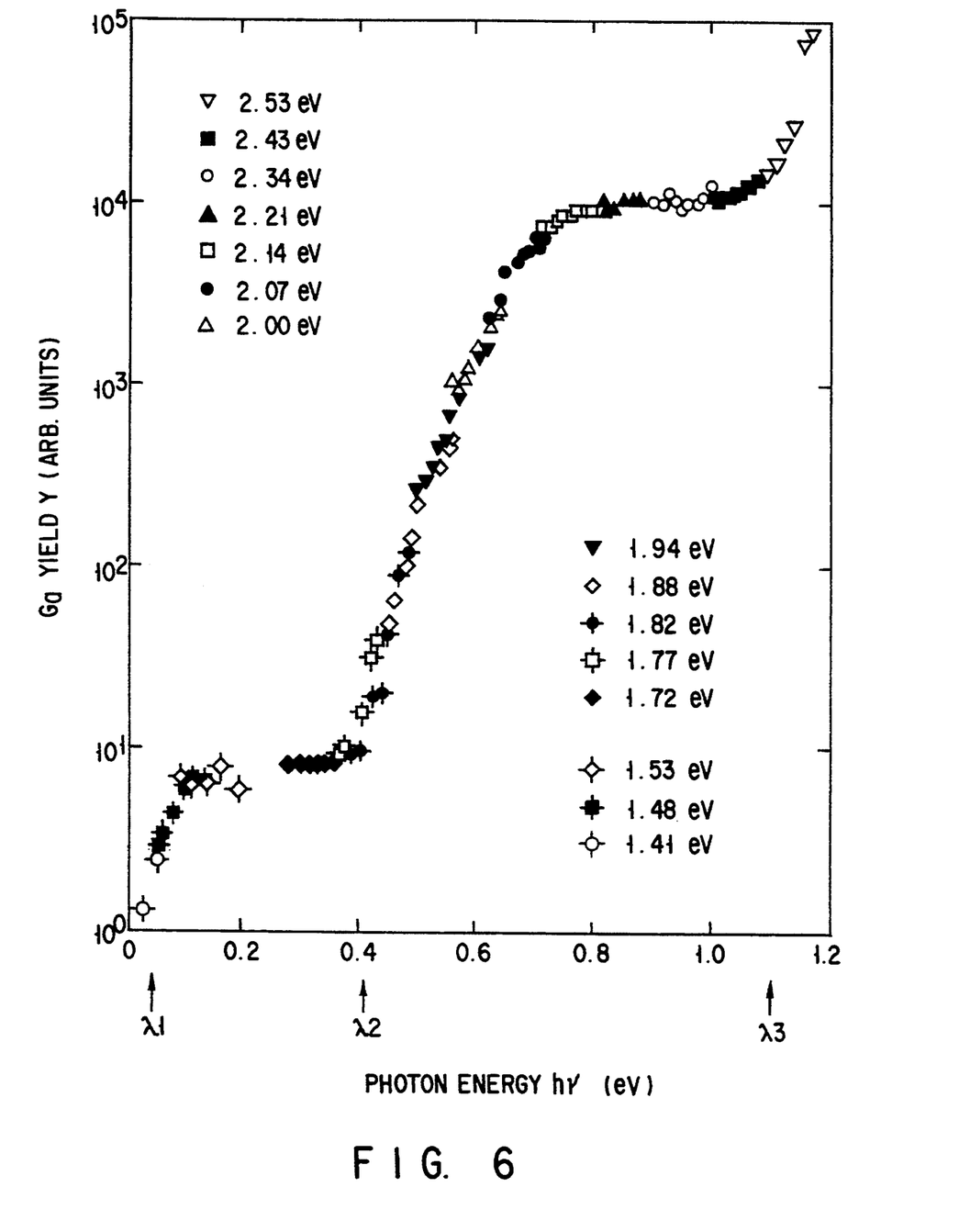
FIG. 6 is a graph showing the dependence of an emission yield Y of GaAs on the difference between the photon energy and the band gap energy.

FIG. 6 shows the energy (wavelength) dependence of the emission yield Y of GaAs. Referring to FIG. 6, a wavelength $\lambda 1$ is a wavelength at which the excitation cross section from the bulk valence band to the bulk conduction band is increased; a wavelength $\lambda 2$, a wavelength at which the excitation cross section from the surface valence band to the bulk conduction band is increased; and a wavelength $\lambda 3$, a wavelength at which the excitation cross section from the surface valence band to the surface conduction band is increased. It is apparent from FIG. 6 that the emission yield is greatly increased above a wavelength at which the electron in the surface valence band can be excited. Therefore, the wavelength of a beam having photon energy higher than that of a beam having the wavelength $\lambda 3$ is preferably used as a laser beam wavelength for the method of the present invention in order to perform measurement with high sensitivity.

Figure 7:
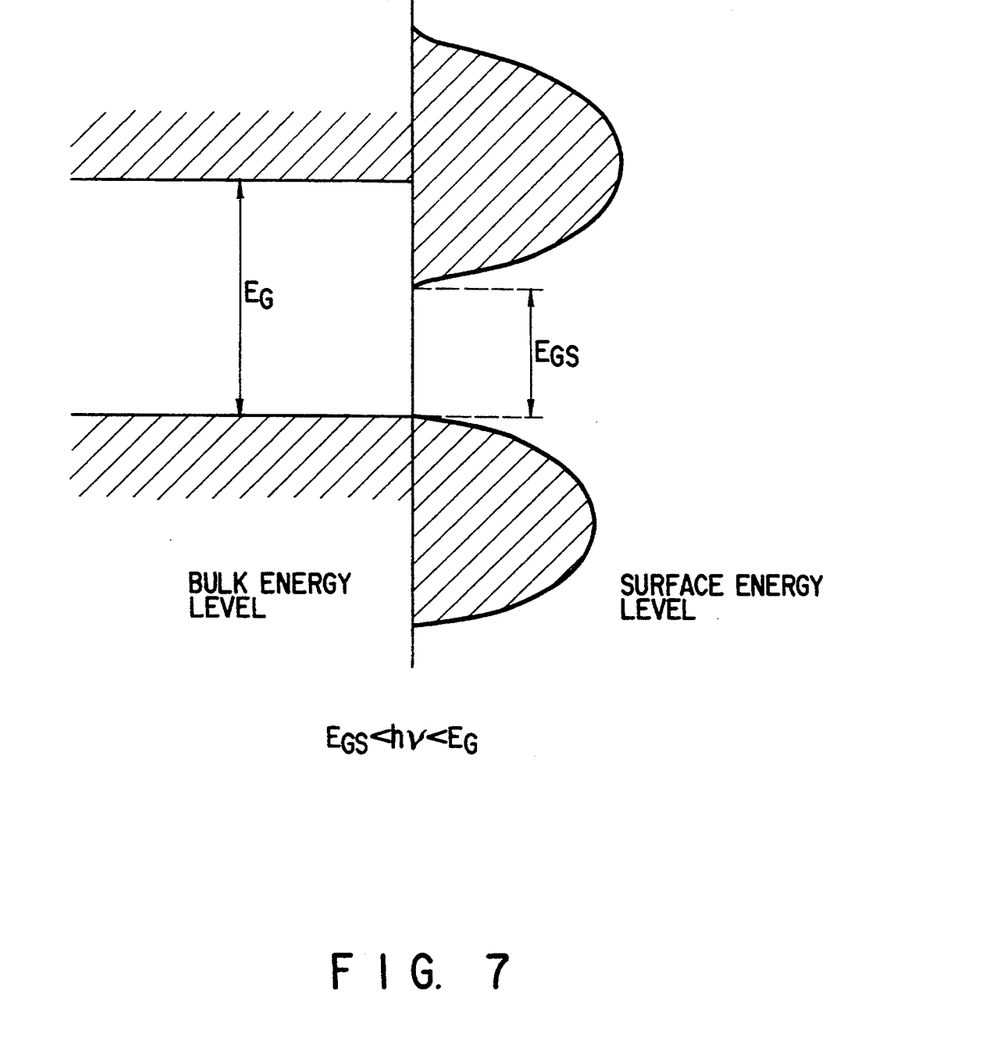
FIG. 7 is an energy band diagram of a GaP surface and a GaP bulk.

GaP has surface and bulk energy levels such as those shown in FIG. 7. As is apparent from FIG. 7, in order to form surface electron-hole pairs in as large a number as possible, it is preferable that a photon energy $h\nu$ be lower than a bulk band gap $E_G$ and higher than a surface band gap $E_{GS}$ ($E_{GS} < h\nu < E_G$). When the photon energy exceeds the bulk band gap $E_G$, excitation from the bulk valence band to the bulk conduction band is increased, resulting in a reduction in yield. Since GaP is subjected to indirect type excitation, the yield of electron-hole pairs in the valence band is small. Therefore, with an energy exceeding the band gap $E_G$, 2D electron-hole pairs may be scattered to the 3D bulk.

In this manner, a proper laser wavelength which allows the formation of a maximum number of surface electron-hole pairs needs to be selected in accordance with a material used.

The present invention is not limited to the above-described embodiment. Various modifications and changes can be made within the spirit and scope of the invention.

What is claimed is:

1. A method of quantitative determination of defect concentration on surfaces, comprising the steps of:
   determining an ablation threshold of a laser fluence with respect to a surface of a sample, manufactured in a high vacuum chamber; and
   determining a quantity of vacancy-type defects by radiating a laser beam having a fluence slightly higher than the ablation threshold on the surface and measuring a first emission yield $Y_1$, corresponding to the quantity of vacancy-type defects, and determining respective quantities of adatom-type and kink-type defects by radiating a pulsed laser beam having a fluence slightly lower than the ablation threshold on the surface of the sample repeatedly to obtain a graph plotting the relationship between a second emission yield $Y_2$, corresponding to the quantities of adatom-type and kink-type defects, and the number of laser pulses, the quantity of the adatom-type defects being obtained by determining an area under a first portion of the graph, and the quantity of kink-type defects being obtained by determining a magnitude of the second emission yield $Y_2$ of a second portion of the graph, the first portion having a steeper negative slope than the second portion.

2. The method according to claim 1, wherein the quantity of vacancy-type defects is obtained by using the equation $$Y_1 = q\phi^n N$$

where q is an emission coefficient, $\phi$ is the laser fluence, n is an exponent, and N is the quantity of vacancy-type defects.

3. The method according to claim 1, wherein the quantity of kink-type defects is obtained by using the equation $$Y_2 = q\phi^n N$$

wherein q is an emission coefficient, $\phi$ is the laser fluence, n is an exponent, and N is the quantity of kink-type defects.

* * * * *